United States Patent [19]

Good

[11] Patent Number: 4,964,800
[45] Date of Patent: Oct. 23, 1990

[54] APPARATUS AND METHOD FOR BENDING DENTAL WIRE

[76] Inventor: Jackson J. Good, 501 N. 13 St., Norfolk, Nebr. 68701

[21] Appl. No.: 328,337

[22] Filed: Mar. 24, 1989

[51] Int. Cl.$^5$ ............................................... A61C 3/00
[52] U.S. Cl. .......................................... 433/3; 433/24; 140/149
[58] Field of Search ........................... 433/2, 3, 24, 75; 140/117, 118, 119, 149

[56] References Cited

U.S. PATENT DOCUMENTS

| | | | |
|---|---|---|---|
| 993,571 | 5/1911 | Berg | 140/117 |
| 3,670,784 | 6/1972 | Ackerman | 140/118 |
| 3,759,302 | 9/1973 | Attenborough | 433/3 |
| 3,906,634 | 9/1975 | Aspel | 433/3 |
| 4,184,259 | 1/1980 | Sosnay | 140/149 |
| 4,656,860 | 4/1987 | Orthuber et al. | 433/3 |

FOREIGN PATENT DOCUMENTS 3032736 12/1981 Fed. Rep. of Germany .......... 433/2

OTHER PUBLICATIONS

Dental Cosmos, "Archograph", 1913, pp. 1028–1032.

Primary Examiner—John J. Wilson
Attorney, Agent, or Firm—Zarley, McKee, Thomte Voorhees & Sease

[57] ABSTRACT

A method for precisely fitting dental wire to brackets on a patient's teeth includes the initial step of measuring the width of the teeth to which the dental wire will be affixed. The width of the teeth are plotted along a straight baseline on a base block, with the desired spacing between the teeth. The dentist must then determine the amount and direction of biasing force necessary to reposition the misaligned teeth to an aligned position. The dental wire is then bent into the appropriate shape using the plotted measurements on the base block to determine the appropriate spacing between the bends and loops in the dental wire. Finally, the dental wire is attached to the brackets on the patient's teeth. The apparatus utilized by the dentist in performing the method of the invention includes a base block as described above, with a straight baseline and a lower edge parallel to the baseline. A T-square-like device is provided with apertures located in an arrangement which will allow pins to be inserted through the T-square into the base block in a predetermined arrangement. Dental wire may then be bent about the pins into the appropriate shape.

2 Claims, 3 Drawing Sheets

APPARATUS AND METHOD FOR BENDING DENTAL WIRE

TECHNICAL FIELD

The present invention relates generally to a method for bending orthodontic wire, and more particularly to an improved method for precisely bending the wire prior to installation of the wire on braces.

BACKGROUND OF THE INVENTION

In orthodontics, braces are formed by placing a series of brackets precisely on the teeth, which will hold a wire strung among all of the brackets. In those locations where one or more teeth are out of alignment, the wire must be bent into helical loops or other shapes to act much as a spring between a pair of brackets. The wire is bent into a specific shape which will place a continuous biasing force between the brackets in the appropriate direction to bring the teeth into alignment. It is the specific shape of the wire loop which continuously exerts force as it attempts to return to its original shape.

Conventionally, the method for attaching this wire to the various brackets on the teeth, was accomplished directly in the patient's mouth. One end of the wire was initially clamped in a first bracket, and then a loop would be formed, if necessary, before inserting the wire into the next adjacent bracket. Not only was this trial-and-error method time consuming, but there was no adequate method of forming uniform or accurate loops in the wire.

It is therefore a general object of the present invention to provide an improved method for precisely bending dental wire.

Another object of the present invention is to provide a method of bending dental wire which may be performed prior to installation in the patient's mouth.

A further object is to provide a method of bending dental wire which allows for precise bending of the wire into the appropriate shape which will produce the desired amount of force between each of the teeth.

Still another object of the present invention is to provide an apparatus for bending dental wire.

Still a further object of the present invention is to provide an apparatus for bending dental wire which allows the user to quickly and precisely bend the wire as desired.

Yet a further object of the present invention is to provide an apparatus for bending dental wire which is simple to use and of economic construction.

These and other objects of the present invention will be apparent to those skilled in the art.

SUMMARY OF THE INVENTION

The method for precisely fitting dental wire to brackets on a patient's teeth of the present invention includes the initial step of measuring the width of the teeth to which the dental wire will be affixed. The width of the teeth are plotted along a straight baseline on a base block, with the desired spacing between the teeth. The dentist must then determine the amount and direction of biasing force necessary to reposition the misaligned teeth to an aligned position. The dental wire is then bent into the appropriate shape using the plotted measurements on the base block to determine the appropriate spacing between the bends and loops in the dental wire. Finally, the dental wire is attached to the brackets on the patient's teeth.

The apparatus utilized by the dentist in performing the method of the invention includes a base block as described above, with a straight baseline and a lower edge parallel to the baseline. A T-square-like device is provided with apertures located in an arrangement which will allow pins to be inserted through the T-square into the base block in a predetermined arrangement. Dental wire may then be bent about the pins into the appropriate shape. A number of T-squares may be provided with various aperture arrangements which will provide pin arrangements on the base block to allow for various bends and loops in the dental wire. A wire bending apparatus is also provided to assist in bending the wire about the pins. The wire bending apparatus includes a vertical rod having a handle at one end and a specially formed lower end. The lower end has an offset aperture therein which will be mounted on an appropriate pin for rotation of the rod about the pin. A depending lip is offset from the aperture and will receive a portion of the dental wire between the lip and aperture so as to bend the wire about the pin.

DESCRIPTION OF THE PREFERRED EMBODIMENT

Figure 1:
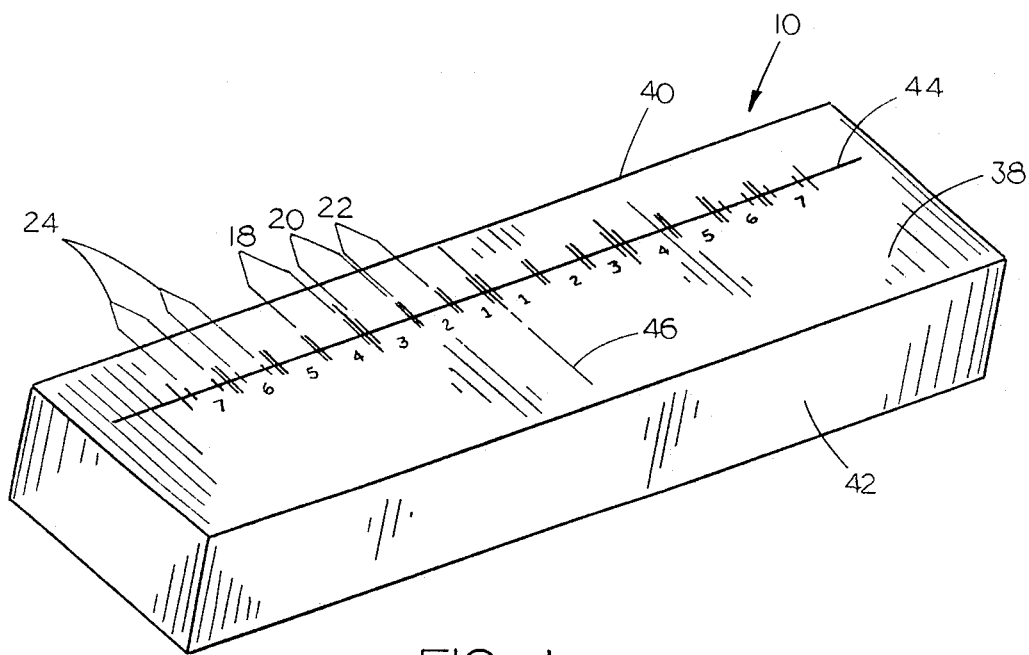
FIG. 1 is a perspective view of a base block, showing an initial step in the method of bending wire of this invention.

Referring now to the drawings, in which similar or corresponding parts are identified with the same reference numeral, and more particularly to FIGS. 1-6, the apparatus utilized in precisely bending wire includes a base block identified generally at 10, a T-square identified generally at 12, a set of pins identified generally at 14, and a wire bender identified generally at 16.

Figure 6:
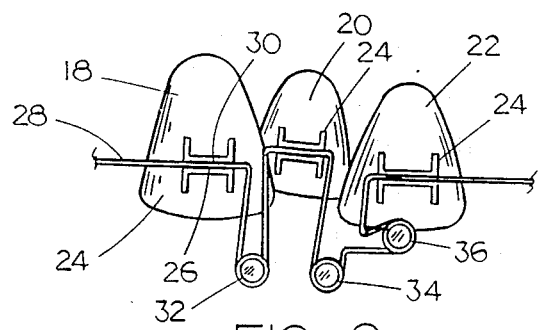
FIG. 6 is an elevational view of misaligned teeth with brackets and dental wire mounted thereon.

Referring now to FIG. 6, a set of teeth 18, 20 and 22 are shown, with middle tooth 20 misaligned. A bracket 24 is mounted on each tooth and includes a horizontally oriented slot 26 which will retain a dental wire 28 therein. The walls 30 lining slot 26 may be crimped in a conventional manner so as to grip the dental wire 28 in the desired position.

Wire 28 extends from bracket 24 on tooth 18 and is formed into a vertical helical loop 32. Wire 28 then extends to bracket 24 on misaligned tooth 20. Wire 28 extends from tooth 20 into a second vertical loop 34, and thence to a horizontal loop 36 before extending to bracket 24 on tooth 22. These helical torsion expansion springs are used to increase arch length for the repositioning of the middle misaligned tooth.

As discussed hereinabove, in the prior art, the orthodontist would first form a loop in the wire and then position the wire 28 with the loop aligned between teeth 18 and 20. The orthodontist would then have to remove and adjust the loop as often as necessary, by trial and error, before reaching the appropriate lengths and desired spring force of vertical spring loop 32. An additional effort would have to be made for the combination vertical and horizontal loops 34 and 36 between teeth 20 and 22. The present invention is designed to greatly simplify the time and effort required to form these loops and install wire 28 on the teeth.

The first step of the method of this invention is to measure and record the width of the teeth and brackets on base block 10, as shown in FIG. 1. Base block 10 includes a top surface 38 with upper and lower longitudinal and parallel edges 40 and 42, respectively. A baseline 44 is drawn longitudinally on top surface 38 and parallel to edges 40 and 42. A centerline 46 is generally centered on top surface 38 and is perpendicular to baseline 44, and indicates the center space between the two front teeth of the individual. The measurement of the width of each tooth is then indicated, measuring from centerline 46 outwardly therefrom, with the appropriate spacing between the teeth also indicated. In this instance, teeth 18, 20 and 22 are indicated as the second, third and fourth tooth to the left of center. The brackets 24 are also indicated appropriately located on each tooth, as shown in FIG. 1. It should be recognized that the recording of the width and spacing of the teeth on the top surface 38 of block 10 will also be the desired spacing and location of the teeth once the dental wire and brackets have accomplished their task of repositioning the teeth. Thus, the formation of bends in wire 28 on block 10 will be the "original position" to which the wire 28 will attempt to return.

Figure 2:
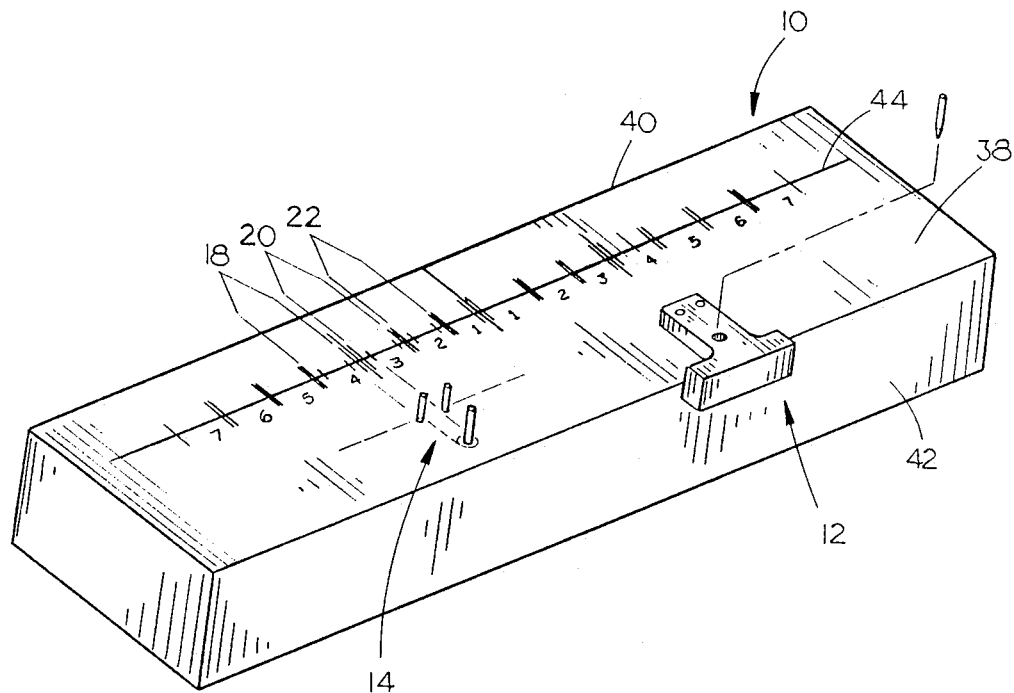
FIG. 2 is a perspective view of the block of FIG. 1, showing a second step in the method of bending wire of this invention.
Figure 7:
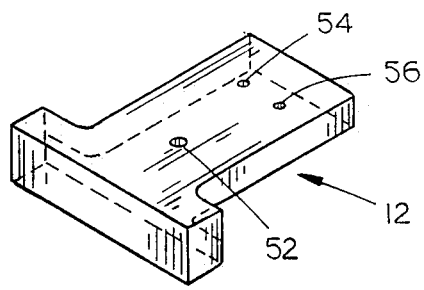
FIG. 7 is a perspective view of a T-square utilized in the method of the present invention.
Figure 8:
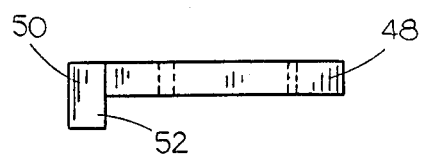
FIG. 8 is a side elevational view of the T-square of FIG. 7.
Figure 9:
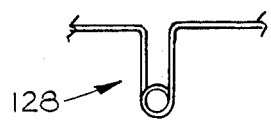
FIG. 9 is a wire formed utilizing the T-square of FIGS. 7-8.

Referring now to FIG. 2, a T-square 12 is provided having a series of apertures therein utilized to locate pins 14 in the desired arrangement. As shown in FIGS. 7 and 8, T-square 12 includes a stem portion 48 extending perpendicularly from an elongated head portion 50. Head portion 50 has a thickness greater than that of stem portion 48 such that a lower end 52 thereof depends downwardly below stem portion 48. Depending portion 52 will slide along the edge 42 of block 10 parallel to baseline 44 as shown in FIGS. 1 and 2.

The T-square of FIG. 7 has two types of apertures extending through stem portion 48—namely, a single large aperture 52 and a pair of smaller apertures 54 and 56. As shown in FIG. 2, large aperture 52 will be used to locate a large pin 58 for use in forming a helical loop.

Small apertures 54 and 56 are utilized to set small pins 60 and 62, which are utilized to bend the wire at a 90° angle. In the instant case, shown at FIG. 2, the stem 48 of T-square 12 is in alignment with the center of the space between teeth 18 and 20. Large pin 58 and small pins 60 and 62 are then hammered into block 10 through the appropriate apertures in T-square 12. T-square 12 may then be removed and repositioned as desired. It can be seen that small pins 60 and 62 are generally aligned with one edge of each bracket 24 on teeth 18 and 20, and large pin 58 is centered therebetween, such that a wire bent around small pins 60 and 62 and looped around large pin 58 will form a vertical helical loop with parallel legs. Once wire 28 is affixed to brackets 24 on teeth 18 and 20, the resiliency of the wire will slowly reposition teeth 18 and 20 until it resumes the "original position" indicated in broken lines on block 10 in FIG. 2.

Figure 3:
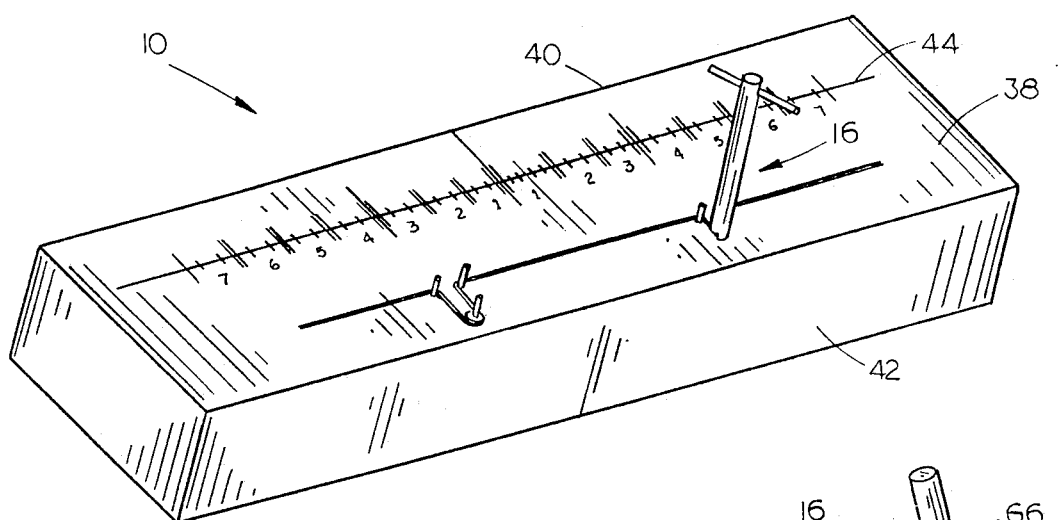
FIG. 3 is a perspective view of the block of FIG. 1 of this invention, showing a third step in the method of bending wire of this invention.
Figure 4:
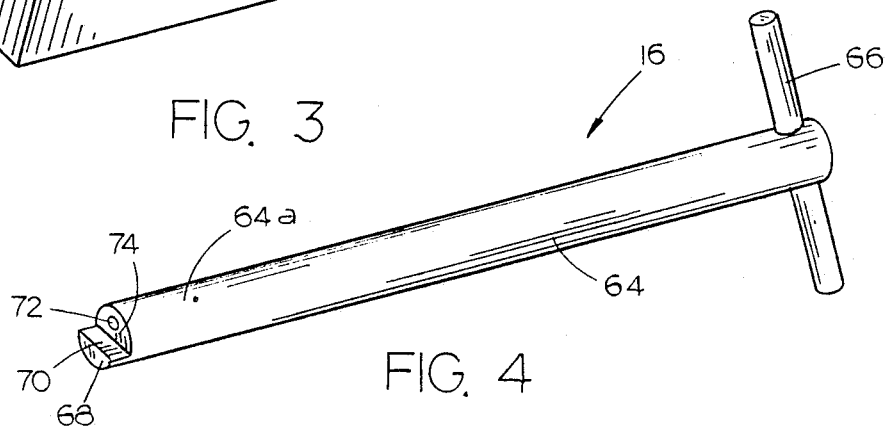
FIG. 4 is a perspective view of the wire bending apparatus of the present invention.
Figure 5:
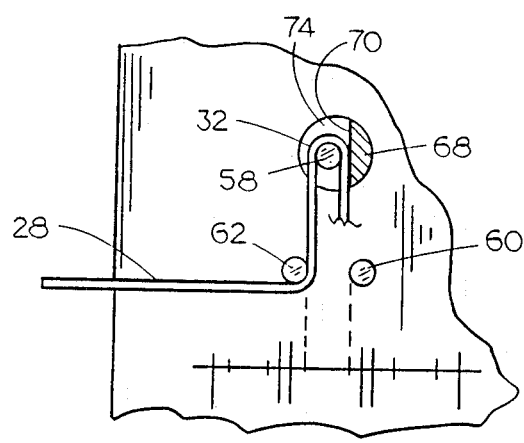
FIG. 5 is a top view of a portion of the base block of FIG. 3, with a sectional view of the end of the wire bender of FIG. 4, showing the use of the wire bender of this invention.

Referring now to FIGS. 3, 4 and 5, the specific method for bending the wire is shown. Wire bender 16 includes a generally cylindrical rod 64 having a handle 66 at one end for leverage in rotating rod 64. The lower end 64a of rod 64 has a portion removed therefrom to form a depending lip 68 with a flat bearing surface 70 which forms a chord of the circle on the bottom of rod 64. Projecting lip 68 forms the smaller portion of the circle intersected by bearing surface 70. An aperture 72 is formed in the larger portion 74 of the bottom end 64a adjacent bearing surface 70. Aperture 72 is offset from the longitudinal axis of rod 64 and parallel thereto. Aperture 72 is located a distance from bearing surface 70 slightly greater than the diameter of the dental wire 28.

In order to form a loop 32, as shown in FIG. 5, dental wire 28 is first bent around pin 62 and placed adjacent pin 58. Rod 64 is then connected to pin 58 with the pin inserted in aperture 72 with bearing surface 70 abutting wire 28 adjacent pin 58. Rod 64 is then rotated such that bearing surface 70 bends wire 28 around pin 58. The end of wire 28 may then be bent around pin 60 and continue to the next set of pins.

Wire bender 16 may utilize a rod 64 having an aperture 72 of either the diameter of large pin 58 or small pin 60, as desired. In this fashion, bends and loops in the dental wire are quickly and easily formed with consistent shape and accuracy.

Figure 10:
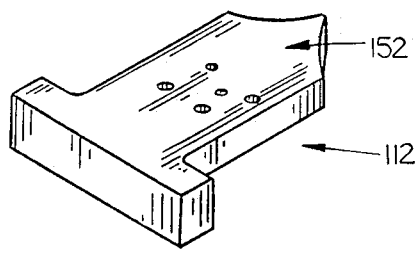
FIG. 10 is a second embodiment of a T-square of the present invention.
Figure 11:
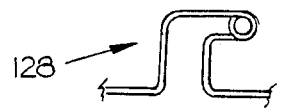
FIG. 11 is a wire formed utilizing the T-square of FIG. 9.
Figure 12:
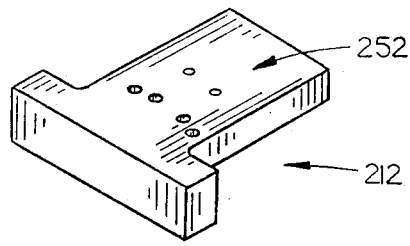
FIG. 12 is a third embodiment of a T-square of the present invention.
Figure 13:
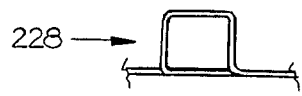
FIG. 13 is a wire formed utilizing the T-square of FIG. 11.
Figure 14:
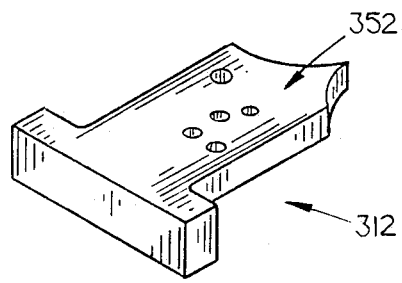
FIG. 14 is a fourth embodiment of a T-square of the present invention.
Figure 15:
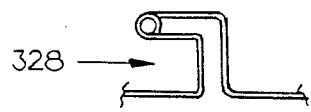
FIG. 15 is a wire formed utilizing the T-square of FIG. 13.

Referring now to FIG. 10, a second embodiment of the T-square is designated generally at 112 and includes a set of apertures 152 arranged so as to enable a dental wire 128 to be formed as shown in FIG. 11. FIG. 12 is a third embodiment of the T-square and is designated generally at 212. Apertures 252 will form dental wire 228 into the form shown in FIG. 13. FIG. 14 is a fourth embodiment of the invention and is designated generally at 312. Aperture set 352 is arranged to form dental wire 328 to the format of FIG. 15.

Whereas the invention has been shown and described in connection with the preferred embodiments thereof, it will be understood that many modifications, substitutions and additions may be made which are within the intended broad scope of the appended claims. For example, many other variations in the pattern of apertures in T-square 12 may be utilized to form the appropriate desired loop in dental wire 28. Thus, there has been shown and described an improved method and apparatus for bending dental wire, which accomplishes at least all of the above-stated objects.

I claim:

1. A method for precisely fitting dental wire to brackets affixed to a patient's teeth in order to reposition misaligned teeth, comprising the steps of:

measuring the width of those teeth to which the dental wire will be affixed;

plotting the width of the teeth, the desired spacing of the teeth, and the width of brackets to be placed on the teeth, along a straight baseline on a base block;

determining the type of biasing force necessary to reposition the misaligned teeth into an aligned position;

bending said dental wire into the appropriate shape to produce the determined biasing force, using the plotted measurements on said base block to determine the appropriate spacing of the bends;

mounting pins on said base block in the locations where said bending step will occur, the pins being mounted such that the dental wire may be bent therearound;

said bending step including bending the wire around said pins to form the appropriate shape in the wire;

providing a jig means with apertures therein located to provide a guide for a predetermined arrangement of said pins;

locating said jig means in those locations on the base block where the dental wire is to be bent;

said step of mounting said pins including the step of inserting the pins through the apertures in said jig means and removing the jig means after mounting the pins; and affixing the bent dental wire to brackets on the patient's teeth.

2. The method of claim 1, further comprising the steps of:

providing a wire bending apparatus for producing uniform and consistent bends in the dental wire, said wire bending apparatus including a depending lip; and wherein the step of bending the wire includes the steps of:

placing the wire bending apparatus on a predetermined pin with a portion of the dental wire between the depending lip and the pin;

rotating the wire bending apparatus such that said lip bends the wire around the pin to a predetermined angle.

* * * * *